(12) United States Patent
Nicholas et al.

(10) Patent No.: US 7,982,082 B1
(45) Date of Patent: Jul. 19, 2011

(54) PROCESS FOR ALKYLATION OF AROMATIC HYDROCARBONS USING UZM-35

(75) Inventors: Christopher P Nicholas, Evanston, IL (US); Deng-Yang Jan, Elk Grove Village, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/820,102

(22) Filed: Jun. 21, 2010

(51) Int. Cl.
*C07C 2/66* (2006.01)
(52) U.S. Cl. ...................................................... 585/467
(58) Field of Classification Search .................... 585/467
See application file for complete search history.

(56) References Cited

U.S. PATENT DOCUMENTS

| | | | |
|---|---|---|---|
| 4,440,871 A * | 4/1984 | Lok et al. ...................... | 502/214 |
| 4,910,006 A | 3/1990 | Zones et al. | |
| 4,963,337 A | 10/1990 | Zones | |
| 5,512,267 A | 4/1996 | Davis et al. | |
| 6,049,018 A | 4/2000 | Calabro et al. | |
| 6,419,895 B1 | 7/2002 | Lewis et al. | |
| 6,713,041 B1 | 3/2004 | Moscoso et al. | |
| 6,756,030 B1 | 6/2004 | Rhode et al. | |
| 7,578,993 B2 | 8/2009 | Lewis et al. | |

OTHER PUBLICATIONS

Lobo, CIT-1: A New Molecular Sieve with Intersecting Pores Bounded by 10- and12-Rings, Journal of American Chemical Society, 1995, pp. 3766-3779, vol. 117.
Wright, Synthesis and Structure of Novel Large-pore Microporous Magnesium-containing Aluminophosphate, Journal of the Chemical Society, Chemical Communications, 1993, pp. 633-635, Issue 7.
Muncaster, An in Situ Microcrystal X-ray Diffraction Study of the Synthetic Aluminophosphate Zeotypes DAF-1 and CoAPSO-44, Chemistry of Materials, 1999, pp. 158-163, vol. 11.

* cited by examiner

*Primary Examiner* — Thuan Dinh Dang
(74) *Attorney, Agent, or Firm* — Maryann Maas

(57) ABSTRACT

Alkylation processes such as the alkylation of aromatics, are catalyzed by the UZM-35 family of crystalline aluminosilicate zeolitic compositions represented by the empirical formula:

$$M_m^{n+}R_r^+Al_{(1-x)}E_xSi_yO_z$$

where M represents a combination of potassium and sodium exchangeable cations, R is a singly charged organoammonium cation such as the dimethyldipropylammonium cation and E is a framework element such as gallium. These UZM-35 zeolitic compositions are active and selective in alkylation processes.

20 Claims, No Drawings

PROCESS FOR ALKYLATION OF AROMATIC HYDROCARBONS USING UZM-35

FIELD OF THE INVENTION

The present invention relates to the use of a zeolitic UZM-35 composition in a process for the alkylation of aromatic hydrocarbons, in particular for the production of ethylbenzene or cumene. In the alkylation process, the zeolitic UZM-35 composition comprises a MSE type zeolite, a MFI type zeolite and an ERI type zeolite. The zeolitic UZM-35 composition may be present in the catalyst as an unmodified zeolitic UZM-35 composition or as a modified UZM-35 composition. The UZM-35 containing catalyst may take one of several forms, including for example, a spherical oil-dropped catalyst or an extruded catalyst.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Topological zeolite structures are described in *Atlas of Zeolite Framework Types*, which is maintained by the International Zeolite Association Structure Commission at http://www.iza-structure.org/databases/. Zeolites can be used as catalysts for hydrocarbon conversion reactions, which can take place on outside surfaces as well as on internal surfaces within the pore.

The alkylation of aromatic hydrocarbons such as benzene with light olefins such as ethylene and propylene is a very important process in a petrochemical refinery. The production of ethylbenzene is used to provide a feedstock for styrene production, while alkylation of benzene with propylene produces isopropylbenzene (cumene). Cumene is an important feedstock to make phenol as well as a good gasoline blending component. These alkylation processes typically use a catalyst composed of one of or a combination of 12-ring and 10-ring zeolites structure types such as FAU, BEA, MWW, and MFI to enable high conversion and high selectivity to alkylated benzenes. In all these alkylation processes, new catalysts are continuously needed with high overall conversion of the feedstock and good selectivity to alkylated benzenes.

Especially advantageous would be a commercially utilizable catalyst containing 12-membered rings and 10-membered rings in the same 3-dimensional structure. Commercial utility is typically seen in aluminosilicate structures which are synthesized in hydroxide media with readily available structure directing agents. Zeolites which contain both 12-membered and 10-membered rings in 3-dimensional structures belong to the CON, DFO, IWR, IWW and MSE structure types. The synthesis of CIT-1, a zeolite of the CON structure type, is described in U.S. Pat. No. 5,512,267 and in J. Am. Chem. Soc. 1995, 117, 3766-79 as a borosilicate form. After synthesis, a subsequent step can be undertaken to allow substitution of Al for B. The zeolites SSZ-26 and SSZ-33, also of the CON structure type are described in U.S. Pat. No. 4,910,006 and U.S. Pat. No. 4,963,337 respectively. SSZ-33 is also described as a borosilicate. All 3 members of the CON structure type use very complicated, difficult to synthesize structure directing agents which make commercial utilization difficult. The known member of the DFO structure type is DAF-1 which is described as an aluminophosphate in Chem. Commun. 1993, 633-35 and in Chem. Mater. 1999, 11, 158-63. Zeolites from the IWR and IWW structure types are synthesized only in hydrofluoric acid containing synthesis routes, making commercial utilization difficult.

One particular zeolite of the MSE structure type, designated MCM-68, was disclosed by Calabro et al. in 1999 (U.S. Pat. No. 6,049,018). This patent describes the synthesis of MCM-68 from dication directing agents, N,N,N',N'-tetraalkylbicyclo[2.2.2]oct-7-ene-2R,3S:5R,6S-dipyrrolidinium dication, and N,N,N',N'-tetraalkylbicyclo[2.2.2]octane-2R,3S:5R,6S-dipyrrolidinium dication. MCM-68 was found to have at least one channel system in which each channel is defined by a 12-membered ring of tetrahedrally coordinated atoms and at least two further independent channel systems in which each channel is defined by a 10-membered ring of tetrahedrally coordinated atoms wherein the number of unique 10-membered ring channels is twice the number of 12-membered ring channels.

Applicants have successfully prepared a new family of materials designated UZM-35. The topology of the primary component of the family of materials is similar to that observed for MCM-68. The materials are prepared via the use of simple, commercially available structure directing agents, such as dimethyldipropylammonium hydroxide, in concert with small amounts of $K^+$ and $Na^+$ together using the Charge Density Mismatch Approach to zeolite synthesis (U.S. Pat. No. 7,578,993).

The alkylation of benzene with ethylene can be performed in gas phase conditions where all the reactants are in the gaseous phase while passing over the solid catalyst or in liquid phase conditions where at least the benzene is present in the liquid phase while passing over the solid catalyst. The UZM-35 family of materials is capable of catalyzing the alkylation of benzene with ethylene in either commercially relevant condition.

The UZM-35 family of materials is able to provide and maintain high conversion of propylene and high selectivity to isopropylbenzene during alkylation of benzene with propylene due to its particular pore geometry and framework Si/Al ratio. The UZM-35 composition contains significant amounts of Al in the tetrahedral framework, with the mole ratio of Si/Al ranging from about 2 to about 12.

SUMMARY OF THE INVENTION

The present invention relates to a process of aromatic alkylation using a catalyst comprising an aluminosilicate zeolitic UZM-35 composition. The process comprises contacting olefinic and alkylatable aromatic hydrocarbons with the UZM-35 composition at alkylation conditions to give an alkylated aromatic product.

The UZM-35 is a microporous crystalline zeolitic composition having a three-dimensional framework of at least $AlO_2$ and $SiO_2$ tetrahedral units and an empirical composition in the as synthesized and anhydrous basis expressed by an empirical formula of:

$$M_m^+R_r^+Al_{1-x}E_xSi_yO_z$$

where M represents a combination of potassium and sodium exchangeable cations, "m" is the mole ratio of M to (Al+E) and varies from about 0.05 to about 3, R is a singly charged organoammonium cation selected from the group consisting of dimethyldipropylammonium ($DMDPA^+$), dimethyldiisopropylammonium ($DMDIP^+$), choline, ethyltrimethylammonium ($ETMA^+$), diethyldimethylammonium ($DEDMA^+$), trimethylpropylammonium, trimethylbutylammonium, dimethyldiethanolammonium, tetraethylammonium ($TEA^+$), tetrapropylammonium ($TPA^+$), methyltripropylammonium, and mixtures thereof, "r" is the mole ratio of R to (Al+E) and has a value of about 0.25 to about 2.0, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m+r+3+4\cdot y)/2$$

and is characterized in that it has the x-ray diffraction pattern having at least the d-spacings and intensities set forth in Table A

TABLE A

| 2θ | d (Å) | I/Io % |
|---|---|---|
| 6.45-6.8 | 13.7-13 | m |
| 6.75-7.13 | 13.1-12.4 | m-vs |
| 7.86-8.26 | 11.25-10.7 | m |
| 8.64-9.04 | 10.23-9.78 | m |
| 9.51-10.09 | 9.3-8.77 | m-vs |
| 10.62-11.23 | 8.33-7.88 | w-m |
| 13.4-14.22 | 6.61-6.23 | w-m |
| 14.76-15.55 | 6-5.7 | w |
| 17.63-18.37 | 5.03-4.83 | w |
| 19.17-19.91 | 4.63-4.46 | w-m |
| 19.64-20.56 | 4.52-4.32 | m |
| 20.18-21.05 | 4.4-4.22 | w-m |
| 20.7-21.57 | 4.29-4.12 | w-m |
| 21.36-22.28 | 4.16-3.99 | vs |
| 22.17-23.6 | 4.01-3.77 | m-s |
| 24.12-25.23 | 3.69-3.53 | w |
| 25.6-26.94 | 3.48-3.31 | m |
| 26.37-27.79 | 3.38-3.21 | m |
| 27.02-28.42 | 3.3-3.14 | m |
| 27.53-28.89 | 3.24-3.09 | m |
| 28.7-30.09 | 3.11-2.97 | m |
| 29.18-30.72 | 3.06-2.91 | w-m |
| 30.19-31.73 | 2.96-2.82 | m |
| 30.83-32.2 | 2.9-2.78 | w |
| 32.81-34.22 | 2.73-2.62 | w |
| 35.63-36.99 | 2.52-2.43 | w |
| 41.03-42.86 | 2.2-2.11 | w |
| 44.18-45.83 | 2.05-1.98 | w |
| 44.87-46.57 | 2.02-1.95 | w |
| 46.07-47.35 | 1.97-1.92 | w |
| 48.97-50.42 | 1.86-1.81 | w | and is thermally stable up to a temperature of greater than 400° C. in one embodiment and 600° C. in another embodiment. When using a the Rietveld refinement method described in J. Appl. Cryst. (1969) 2, 65-71) the x-ray diffraction pattern has at least the d-spacings and intensities set forth in Table A'

TABLE A'

| 2θ | d (Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w |

The crystalline microporous zeolitic composition described above may be synthesized by forming a reaction mixture containing reactive sources of M, R, Al, Si and optionally E and heating the reaction mixture at a temperature of about 150° C. to about 200° C., or about 165° C. to about 185° C., for a time sufficient to form the composition, the reaction mixture having a composition expressed in terms of mole ratios of the oxides of:

$$aM_2O:bR_{2/p}O:1-cAl_2O_3:cE_2O_3:dSiO_2:eH_2O$$

where "a" has a value of about 0.05 to about 1.25, "b" has a value of about 1.5 to about 40, "p" is the weighted average valance of R and varies from 1 to about 2, "c" has a value of 0 to about 1.0, "d" has a value of about 4 to about 40, "e" has a value of about 25 to about 4000.

Yet another embodiment of the invention is a catalytic process for alkylation of aromatic hydrocarbons using the above-described composition. The process comprises contacting the light olefin and the aromatic hydrocarbon with the UZM-35 composition at conversion conditions to give an alkylated aromatic hydrocarbon.

DETAILED DESCRIPTION OF THE INVENTION

Applicants have prepared an aluminosilicate zeolitic UZM-35 composition whose main component has a topological structure related to MSE as described in *Atlas of Zeolite Framework Types*, which is maintained by the International Zeolite Association Structure Commission at http://www.iza-structure.org/databases/. As is shown in U.S. application Ser. No. 12/241,302 in detail, UZM-35 material is different from MCM-68 in a number of its characteristics. The microporous crystalline zeolitic UZM-35 composition has an empirical composition in the as-synthesized form and on an anhydrous basis expressed by the empirical formula:

$$M_m^{+}R_r^{+}Al_{1-x}E_xSi_yO_z$$

where M represents a combination of potassium and sodium exchangeable cations. R is a singly charged organoammonium cation, examples of which include but are not limited to the dimethyldipropylammonium cation (DMDPA$^+$), dimethyldiisopropylammonium (DMDIP$^+$), choline [(CH$_3$)$_3$N(CH$_2$)$_2$OH]$^+$, ETMA$^+$, DEDMA$^+$, trimethylpropylammonium, trimethylbutylammonium, dimethyldiethanolammonium, methyltripropylammonium, TEA$^+$, TPA$^+$ and mixtures thereof and "r" is the mole ratio of R to (Al+E) and varies from about 0.25 to about 2.0 while "m" is the mole ratio of M to (Al+E) and varies from about 0.05 to about 3. The mole ratio of silicon to (Al+E) is represented by "y" which varies from about 2 to about 30. E is an element which is tetrahedrally coordinated, is present in the framework and is selected from the group consisting of gallium, iron and boron. The mole fraction of E is represented by "x" and has a value from 0 to about 1.0, while "z" is the mole ratio of O to (Al+E) and is given by the equation:

$$z=(m\cdot n+r+3+4\cdot y)/2.$$

Where M is only one metal, then the weighted average valence is the valence of that one metal, i.e. +1 or +2. However, when more than one M metal is present, the total amount of:
and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

The microporous crystalline zeolitic UZM-35 composition is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals, potassium and sodium, include the halide salts, nitrate salts, acetate salts, and hydroxides of the respective alkali metals. R is an organoammonium cation selected from the group consisting of dimethyldiisopropylammonium, dimethyldipropylammonium, choline, ETMA, DEDMA, TEA, TPA, trimethylpropylammonium, trimethylbutylammonium, dimethyldiethanolammonium and mixtures thereof, and the sources include the hydroxide, chloride, bromide, iodide and fluoride compounds. Specific examples include without limitation dimethyldipropylammonium hydroxide, dimethyldipropylammonium chloride, dimethyldipropylammonium bromide, dimethyldiisopropylammonium hydroxide, dimethyldiisopropylammonium chloride, dimethyldiisopropylammonium bromide, ethyltrimethylammonium hydroxide, diethyldimethylammonium hydroxide, tetraethylammonium hydroxide, tetrapropylammonium hydroxide, and tetrapropylammonium chloride.

Note that during synthesis, the metal M is +1 valence, specifically potassium and sodium. However, in an alternative embodiment, the composition may undergo additional ion exchange steps, post synthesis, to provide a material with one or more metals, M, having a +2 valence.

The reaction mixture containing reactive sources of the desired components can be described in terms of molar ratios of the oxides by the formula:

$$aM_2O:bR_{2/p}O:1-cAl_2O_3:cE_2O_3:dSiO_2:eH_2O$$

where "a" varies from about 0.05 to about 1.25, "b" varies from about 1.5 to about 40, "c" varies from 0 to 1.0, "d" varies from about 4 to about 40, "e" varies from about 25 to about 4000, and "p" is the weighted average valence of R and varies from 1 to about 2. If alkoxides are used, it is preferred to include a distillation or evaporative step to remove the alcohol hydrolysis products. The reaction mixture is now reacted at a temperature of about 150° C. to about 200° C., about 165° C. to about 185° C., or about 170° C. to about 180° C., for a period of about 1 day to about 3 weeks and preferably for a time of about 5 days to about 12 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. It should be pointed out that UZM-35 seeds can optionally be added to the reaction mixture in order to accelerate the formation of the zeolite.

A preferred synthetic approach to make UZM-35 utilizes the charge density mismatch concept, which is disclosed in U.S. Pat. No. 7,578,993 and *Studies in Surface Science and Catalysis*, (2004), Vol. 154A, 364-372. The method disclosed in U.S. Pat. No. 7,578,993 employs quaternary ammonium hydroxides to solubilize aluminosilicate species, while crystallization inducing agents such as alkali and alkaline earth metals and more highly charged organoammonium cations are often introduced in a separate step. Once some UZM-35 seeds have been generated using this approach, the seeds can be used in a single step synthesis of UZM-35, using, for example, a combination of dimethyldiisopropylammonium, dimethyldipropylammonium hydroxide and the alkali cations. The use of commercially available dimethyldipropylammonium hydroxide to prepare UZM-35 composition offers a great economic advantage over the structure directing agents previously employed (N,N,N',N'-tetraalkylbicyclo[2.2.2]oct-7-ene-2R,3S:5R,6S-dipyrrolidinium dication, and N,N,N',N'-tetraalkylbicyclo[2.2.2]octane-2R,3S:5R,6S-dipyrrolidinium dication) to prepare aluminosilicates with the MSE topology. Additionally, dimethyldipropyl ammonium hydroxide can be employed as the hydroxide or the chloride in concert with other inexpensive organoammonium hydroxides using the charge density mismatch concept to reduce costs even further.

The UZM-35 aluminosilicate zeolitic composition, which is obtained from the above-described process, is characterized by the x-ray diffraction pattern, having at least the d-spacings and relative intensities set forth in Table A below.

TABLE A

| 2θ | d (Å) | I/Io % |
|---|---|---|
| 6.45-6.8 | 13.7-13 | m |
| 6.75-7.13 | 13.1-12.4 | m-vs |
| 7.86-8.26 | 11.25-10.7 | m |
| 8.64-9.04 | 10.23-9.78 | m |
| 9.51-10.09 | 9.3-8.77 | m-vs |
| 10.62-11.23 | 8.33-7.88 | w-m |
| 13.4-14.22 | 6.61-6.23 | w-m |
| 14.76-15.55 | 6-5.7 | w |
| 17.63-18.37 | 5.03-4.83 | w |
| 19.17-19.91 | 4.63-4.46 | w-m |
| 19.64-20.56 | 4.52-4.32 | m |
| 20.18-21.05 | 4.4-4.22 | w-m |
| 20.7-21.57 | 4.29-4.12 | w-m |
| 21.36-22.28 | 4.16-3.99 | vs |
| 22.17-23.6 | 4.01-3.77 | m-s |
| 24.12-25.23 | 3.69-3.53 | w |
| 25.6-26.94 | 3.48-3.31 | m |
| 26.37-27.79 | 3.38-3.21 | m |
| 27.02-28.42 | 3.3-3.14 | m |
| 27.53-28.89 | 3.24-3.09 | m |
| 28.7-30.09 | 3.11-2.97 | m |
| 29.18-30.72 | 3.06-2.91 | w-m |
| 30.19-31.73 | 2.96-2.82 | m |
| 30.83-32.2 | 2.9-2.78 | w |
| 32.81-34.22 | 2.73-2.62 | w |
| 35.63-36.99 | 2.52-2.43 | w |
| 41.03-42.86 | 2.2-2.11 | w |
| 44.18-45.83 | 2.05-1.98 | w |
| 44.87-46.57 | 2.02-1.95 | w |
| 46.07-47.35 | 1.97-1.92 | w |
| 48.97-50.42 | 1.86-1.81 | w |

As will be shown in detail in the examples, the UZM-35 material is thermally and catalytically stable up to a temperature of at least 400° C. and in another embodiment, up to about 600° C. The UZM-35 composition as synthesized comprises a MSE topology zeolite, a MFI topology zeolite and an ERI topology zeolite. Typically, the amount of MSE zeolite in the composition will vary from about 55 wt % to about 75 wt. % or from about 55 wt-% to about 90 wt.-%. The amount of MFI zeolite varies from about 20 wt-% to about 35 wt-% of the composition or from about 10 wt-% to about 35 wt.-%, and the amount of ERI zeolite varies from about 3 wt-% to about 9 wt-% of the composition or from about 3 wt-% to about 10 wt.-%. Of course, the sum of the amount of the three zeolites, absent any other impurities, adds up to 100 wt % of the composition.

When using a the Rietveld refinement method described in J. Appl. Cryst. (1969) 2, 65-71) the x-ray diffraction pattern has at least the d-spacings and intensities set forth in Table A'

TABLE A'

| 2θ | d (Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |

TABLE A'-continued

| 2θ | d (Å) | I/Io % |
|---|---|---|
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w |

As synthesized, the UZM-35 material will contain some of the exchangeable or charge balancing cations in its pores. These exchangeable cations can be exchanged for other cations, or in the case of organic cations, they can be removed by heating under controlled conditions. Because UZM-35 composition contains a large pore zeolite, it is also possible to remove some organic cations directly by ion exchange. The UZM-35 composition may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Properties that are modified include porosity, adsorption, Si/Al mole ratio, acidity, thermal stability, and the like.

The UZM-35 composition as outlined above or a modification thereof, is used as a catalyst or catalyst support in various alkylation reactions of aromatic hydrocarbons. The composition preferably is mixed with a binder for convenient formation of catalyst particles in a proportion of about 5 to 100 mass % UZM-35 composition and 0 to 95 mass-% binder, with the UZM-35 composition preferably comprising from about 10 to 90 mass-% of the composite. The binder should preferably be porous, have a surface area of about 5 to about 800 m²/g, and be relatively refractory to the conditions utilized in the hydrocarbon conversion process. Non-limiting examples of binders are alumina, titania, zirconia, zinc oxide, magnesia, boria, silica-alumina, silica-magnesia, chromia-alumina, alumina-boria, aluminophosphates, silica-zirconia, silica, silica gel, and clays. Preferred binders are amorphous silica and alumina, including gamma-, eta-, and theta-alumina, with gamma- and eta-alumina being especially preferred.

The zeolite with or without a binder can be formed into various shapes such as pills, pellets, extrudates, spheres, etc. Preferred shapes are extrudates and spheres. Extrudates are prepared by conventional means which involves mixing of the composition either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50 to about 200° C. and subjected to a calcination procedure at a temperature of about 450 to about 700° C. for a period of about 1 to about 20 hours. This treatment effects conversion of the hydrogel to the corresponding alumina matrix.

The interaction of the feed molecules with the catalyst is of great importance in catalysis. This interaction may be characterized by the contact time. Contact time is calculated by dividing the catalyst volume by the feed flow rate. Lower contact times indicate less interaction of the feed with the catalyst, while higher contact times indicate high interaction of the feed with the catalyst. Selectivity to specific products may be altered by altering the contact time. For reactions such as alkylation of aromatic hydrocarbons, where a feedstock containing an alkylatable hydrocarbon and a stream comprising at least one olefin are both passed over the catalyst, the contact time is calculated using the combined feed rate.

The alkylation and preferably the monoalkylation of aromatic compounds involves reacting an alkylatable aromatic compound with an olefin using the above described zeolitic catalyst. The olefins which can be used in the instant process are any of those which contain from 2 up to about 6 carbon atoms. These olefins may be branched or linear olefins and either terminal or internal olefins. Preferred olefins are ethylene, propylene, butenes and amylenes.

The alkylatable aromatic compounds may be selected from the group consisting of benzene, naphthalene, anthracene, phenanthrene, and substituted derivatives thereof, with benzene and its derivatives being the most preferred aromatic compound. By alkylatable is meant that the aromatic compound can be alkylated by an olefinic compound. The alkylatable aromatic compounds may have one or more of the substituents selected from the group consisting of alkyl groups (having from 1 to about 20 carbon atoms), hydroxyl groups, and alkoxy groups whose alkyl group also contains from 1 up to 20 carbon atoms. Where the substituent is an alkyl or alkoxy group, a phenyl group can also be substituted on the alkyl chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, phenol, cresol, anisole, ethoxy-, propoxy-, butoxy-, pentoxy-, hexoxybenzene, etc.

Reactions involving the alkylation of aromatic hydrocarbons are processes well known in the art and include the production of ethylbenzene and cumene. Specific reaction conditions and the types of feeds which can be used in these processes are set forth in (U.S. Pat. No. 7,498,472, U.S. Pat. No. 7,525,003, U.S. Pat. No. 7,525,004, U.S. Pat. No. 7,420, 098, U.S. Pat. No. 7,525,005, U.S. Pat. No. 7,525,006) which are all hereby incorporated by reference in their entirety. The following examples are presented in illustration of this invention and are not intended as undue limitations on the generally broad scope of the invention as set out in the appended claims.

Reactions involving the alkylation of aromatic hydrocarbons are processes well known in the art and include the production of ethylbenzene and cumene. Specific reaction conditions and the types of feeds which can be used in these processes are set forth in: U.S. Pat. No. 7,498,472, U.S. Pat. No. 7,525,003, U.S. Pat. No. 7,525,004, U.S. Pat. No. 7,420, 098, U.S. Pat. No. 7,525,005, U.S. Pat. No. 7,525,006 which are all hereby incorporated by reference in their entirety. The following examples are presented in illustration of this invention and are not intended as undue limitations on the generally broad scope of the invention as set out in the claims The structure of the UZM-35 zeolitic composition of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$," being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of $100 \times I/I_o$, the above designations are defined as:

w=0-15: m=15-60: s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

An aluminosilicate reaction solution was prepared by first mixing 27.17 g of aluminum hydroxide (27.78 mass-% Al) and 1053.58 g dimethyldipropylammonium hydroxide (18.8 mass-% solution), while stirring vigorously. After thorough mixing, 505.96 g Ludox™ AS-40 (40 mass-% $SiO_2$) was added. The reaction mixture was homogenized for an additional hour with a high speed mechanical stirrer, sealed in a Teflon bottle, and placed in an oven overnight at 100° C. Analysis showed the aluminosilicate solution contained 6.16 wt. % Si and 0.67 wt. % Al (Si/Al molar ratio of 8.83).

A 1200 g portion of the above aluminosilicate solution was continuously stirred. A composite aqueous solution containing 28.56 g of KOH and 3.6 g of NaOH dissolved in 150 g distilled water, was added, drop-wise, to the aluminosilicate solution. After the addition was completed, the resulting reaction mixture was homogenized for 1 hour, transferred to a 2000 ml Parr stainless steel autoclave which was heated to 175° C. and maintained at that temperature for 216 hrs. The solid product was recovered by centrifugation, washed with de-ionized water, and dried at 100° C.

The solid product was recovered by centrifugation, washed with de-ionized water and dried at 95° C. The product was identified as UZM-35 by xrd. Representative diffraction lines observed for the product are shown in Table 1. The product composition was determined by elemental analysis to consist of the following mole ratios: Si/Al=7.92, Na/Al=0.1, K/Al=0.48.

TABLE 1

| 2θ | d (Å) | I/Io% |
|---|---|---|
| 6.65 | 13.26 | m |
| 6.95 | 12.69 | m |
| 8.10 | 10.90 | m |
| 8.87 | 9.95 | m |
| 9.76 | 9.05 | m |
| 10.83 | 8.13 | w |
| 13.76 | 6.43 | w |
| 15.22 | 5.81 | w |
| 18.00 | 4.92 | w |
| 19.46 | 4.55 | m |
| 19.62 | 4.52 | m |
| 20.06 | 4.42 | m |
| 20.63 | 4.3 | m |
| 21.1 | 4.20 | m |
| 21.76 | 4.08 | vs |
| 21.92 | 4.05 | m |
| 22.07 | 4.03 | m |
| 22.55 | 3.93 | m |
| 22.73 | 3.90 | m |
| 23.08 | 3.85 | s |
| 23.42 | 3.79 | m |
| 23.51 | 3.77 | m |
| 24.04 | 3.69 | m |
| 24.53 | 3.62 | w |
| 25.9 | 3.43 | m |
| 25.99 | 3.42 | w |
| 26.27 | 3.38 | m |
| 26.92 | 3.3 | m |
| 27.57 | 3.23 | m |
| 27.76 | 3.21 | m |
| 28.17 | 3.16 | m |
| 28.86 | 3.09 | w |
| 29.27 | 3.04 | m |
| 29.72 | 3.00 | w |
| 30.26 | 2.95 | w |
| 30.91 | 2.88 | m |
| 31.38 | 2.84 | w |
| 33.61 | 2.68 | w |
| 34.65 | 2.58 | w |
| 35.43 | 2.53 | w |
| 36.18 | 2.48 | w |
| 41.77 | 2.16 | w |
| 44.7 | 2.02 | w |
| 45.32 | 1.99 | w |
| 45.63 | 1.98 | w |
| 46.55 | 1.94 | w |
| 47.62 | 1.90 | w |
| 47.94 | 1.89 | w |
| 49.70 | 1.83 | w |
| 51.06 | 1.78 | w |

Example 2

The UZM-35 of example 1 was calcined at 540° C. for 10 hrs under nitrogen and then air. Representative diffraction lines observed for the product are shown in Table 2.

TABLE 2

| 2θ | d (Å) | I/Io% |
|---|---|---|
| 6.72 | 13.13 | m |
| 7.02 | 12.57 | vs |
| 8.0 | 11.04 | m |
| 8.2 | 10.77 | m |
| 8.3 | 10.64 | m |
| 8.98 | 9.83 | m |
| 9.87 | 8.94 | vs |
| 11.00 | 8.03 | m |
| 11.29 | 7.82 | w |
| 13.85 | 6.38 | m |
| 14.17 | 6.24 | w |
| 14.95 | 5.91 | w |
| 15.04 | 5.88 | w |
| 17.72 | 4.99 | w |
| 17.90 | 4.95 | w |
| 19.56 | 4.53 | m |
| 19.64 | 4.51 | m |
| 19.70 | 4.50 | m |
| 20.16 | 4.40 | m |
| 20.64 | 4.29 | w |
| 21.15 | 4.19 | w |
| 21.86 | 4.06 | vs |
| 21.98 | 4.04 | s |
| 22.07 | 4.02 | m |
| 22.62 | 3.92 | m |
| 22.72 | 3.91 | s |
| 23.27 | 3.91 | vs |
| 24.08 | 3.69 | m |
| 24.69 | 3.60 | w |
| 25.29 | 3.51 | w |
| 26.28 | 3.38 | m |
| 27.12 | 3.28 | m |
| 27.66 | 3.22 | m |
| 28.28 | 3.15 | m |
| 28.98 | 3.07 | w |
| 29.36 | 3.03 | m |
| 29.99 | 2.97 | w |
| 30.38 | 2.93 | m |
| 31.02 | 2.88 | m |
| 31.54 | 2.83 | w |
| 33.46 | 2.67 | w |
| 34.68 | 2.58 | w |
| 35.07 | 2.55 | w |
| 35.84 | 2.50 | w |
| 36.29 | 2.47 | w |
| 39.37 | 2.28 | w |
| 41.92 | 2.15 | w |
| 44.96 | 2.01 | w |
| 45.72 | 1.98 | w |
| 46.74 | 1.94 | w |
| 47.82 | 1.9 | w |
| 48.13 | 1.88 | w |
| 49.75 | 1.83 | W |

Example 3

The UZM-35 of example 2 then was ammonium ion-exchanged to exchange Na or K cations for $NH_4$.

Comparative Example 4

A sample of H-MFI zeolite, bound 66/34 with $AlPO_4$ was obtained. The catalyst consists of 1/16" diameter spheres. The $SiO_2/Al_2O_3$ ratio of the MFI is 38.

Example 5

The UZM-35 of Example 3 was pressed and meshed to 20-40 mesh prior to testing. For alkylation of benzene with propylene to form cumene, 15 mL of meshed catalyst is mixed with 10 mL of gamma alumina of 20-40 mesh and loaded into the reactor. The reactor was pressurized to 500 psig with $N_2$ and benzene flow was then started. Once the reactor attained the target temperature, the propylene was introduced. Results of the cumene synthesis tests are shown in Table 3.

TABLE 3

| Catalyst | Temperature (° C.) | LHSV (olefin) | LHSV (C$_6$H$_6$) | B/O ratio | Conversion (mol %) | Cumene Selectivity | n-Pr benzene Selectivity | DIPB Selectivity | Heavy Selectivity |
|---|---|---|---|---|---|---|---|---|---|
| Example 5 UZM-35 | 148 | 0.7 | 5.4 | 7 | ~100 | 84.8% | 600 ppm | 7.2% | 8% |
| Example 5 UZM-35 | 148 | 1.1 | 4.9 | 4 | ~100 | 76.3% | 800 ppm | 11.3% | 12.4% |
| Example 5 UZM-35 | 148 | 0.9 | 6.6 | 7 | ~100 | 86.0% | 600 ppm | 7.2% | 6.8% |
| Example 5 UZM-35 | 148 | 2.0 | 5.4 | 2.5 | ~100 | 68.8% | 1550 ppm | 14.0% | 17.2% |

Not only does the UZM-35 catalyst exhibit good selectivity to cumene under these conditions, it is remarkably stable. In 16 hours of reaction at the first condition, no evidence of deactivation was observed. Indeed, over the 60 total hours of reaction time, no deactivation in conversion or change in selectivity due to deactivation was noted.

Comparative Example 6

The MFI catalyst of Example 4, 10.3 mL was loaded into the reactor. The reactor was pressurized to 500 psig with N$_2$ and benzene flow was started. Once the reactor attained the target temperature, the ethylene containing gas was introduced. The gas feed consisted of 77% CH$_4$ and 23% C$_2$H$_4$. Results of the ethylbenzene synthesis tests are shown in Table 4.

Example 7

The UZM-35 of Example 3 then pressed and meshed to 20-40 mesh prior to testing. For alkylation of benzene with ethylene, 15 mL of meshed catalyst was loaded into the reactor. The reactor was pressurized to 500 psig with N$_2$. Benzene flow was started and once the reactor was up to temperature, the ethylene containing gas was introduced. The gas feed consisted of 77% CH$_4$ and 23% C$_2$H$_4$. Results of the ethylbenzene synthesis tests are shown in Table 4.

TABLE 4

Ethylbenzene Synthesis

| Catalyst | Temperature (° C.) | WHSV (olefin) | WHSV (C$_6$H$_6$) | B/O ratio | Conversion (wt %) | Ethylbenzene Selectivity | DIEB Selectivity | TIEB Selectivity | Other Selectivity |
|---|---|---|---|---|---|---|---|---|---|
| Example 6 MFI | 250 | 1.0 | 8.34 | 3 | 3% | 80% | 0.25% | ~0% | 19.8% |
| Example 6 MFI | 279 | 1.0 | 8.34 | 3 | 8.8 | 86% | 1.25% | ~0% | 12.8% |
| Example 6 MFI | 305 | 1.0 | 8.34 | 3 | 18.5 | 79% | 3.9% | ~0% | 17.1% |
| Example 7 UZM-35 | 190 | 1.0 | 8.36 | 3 | 6.6 | 89% | 5.6% | 0.5% | 4.9% |
| Example 7 UZM-35 | 219 | 1.0 | 19.5 | 7 | 19 | 88% | 4.7% | 0.2% | 7.1% |

As can be seen from the results in Table 4, the UZM-35 family of catalysts is active at much lower temperatures than typical MFI catalysts, which is used in commercial EB synthesis, for ethylbenzene synthesis. In addition, the selectivity of UZM-35 catalysts toward ethylbenzene is better than that of MFI. For the MFI catalyst, other selectivity is composed largely of ethylene oligomers, 2-butylbenzene, cumene and light alkanes with trace amounts of tert-butylbenzene and xylenes and, in the 305° C. temperature data, toluene, ethyltoluenes and trimethylbenzenes. For the UZM-35 catalyst, the other selectivity is composed of largely of 2-butylbenzene and ethylene oligomers, with trace amounts of cumene and tert-butylbenzene.

Example 8

An aluminosilicate reaction solution was prepared by first mixing 86.33 g of aluminum hydroxide (26.97 mass-% Al) and 1437.67 g of dimethyldipropylammonium hydroxide (40.66 mass-% solution), while stirring vigorously. After thorough mixing, 1366.88 g Ludox™ AS-40 (SiO$_2$, mass-40%) was added. The reaction mixture was homogenized for 20 minutes with a high-speed mechanical stirrer, the aluminosilicate colloidal solution was continuously stirred and an aqueous solution containing 83.04 g of KOH and 17.38 g of NaOH dissolved in 808.7 g H$_2$O, was added, drop wise, to the aluminosilicate solution. After the addition was completed, the resulting reaction mixture was homogenized for ½ hour, transferred to (3) 2000 ml Parr stainless steel autoclave which were heated to 175° C. and maintained at that temperature for 9 days. The solid products were recovered by filtration, washed with de-ionized water, and dried at 100° C.

The product resulting from this reaction was identified by x-ray diffraction (Rietveld refinement method described in J. Appl. Cryst. (1969) 2, 65-71) to be a UZM-35 composition of 72.1 wt-% MSE type zeolite with a lattice parameter of 18.372 angstroms for a and 20.285 angstroms for c; 24.1 wt-% MFI zeolite with a lattice parameter of 20.101 angstroms for a, 19.862 angstroms for b and 13.402 for c, and 3.7 wt-% ERI zeolite with a lattice parameter of 13.222 angstroms for a and 14.900 angstroms for c. Chemical analysis gave a product composition of mole ratio Si/Al=8.9. BET Surface area was determined to be 408 m2/g and micropore volume was 0.197 cc/g. Representative diffraction lines observed for the product are shown in Table 5.

TABLE 5

| 2θ | d (Å) | I/Io % |
|---|---|---|
| 6.5 | 13.58 | m |
| 6.8 | 12.99 | s |
| 7.79 | 11.32 | m |
| 8.07 | 10.93 | m |
| 8.719 | 10.13 | m |
| 9.63 | 9.17 | s |
| 10.75 | 8.21 | w |
| 13.63 | 6.49 | w |
| 14.74 | 6.00 | w |
| 15.56 | 5.69 | w |
| 15.86 | 5.58 | w |
| 19.46 | 4.55 | m |
| 19.899 | 4.45 | m |
| 20.518 | 4.32 | m |
| 20.94 | 4.23 | w |
| 21.618 | 4.1 | vs |
| 21.799 | 4.07 | s |
| 22.399 | 3.96 | m |
| 22.93 | 3.87 | s |
| 23.299 | 3.81 | m |
| 23.78 | 3.73 | m |
| 24.82 | 3.58 | w |
| 25.76 | 3.45 | w |
| 26.09 | 3.41 | m |
| 26.74 | 3.33 | m |
| 27.42 | 3.24 | m |
| 28.04 | 3.17 | w |
| 29.10 | 3.06 | w |
| 29.54 | 3.02 | w |
| 29.75 | 2.99 | w |
| 30.13 | 2.96 | m |
| 30.73 | 2.9 | m |
| 31.47 | 2.83 | w |
| 33.19 | 2.69 | w |
| 34.46 | 2.6 | w |
| 35.18 | 2.54 | w |
| 35.59 | 2.51 | w |
| 36.04 | 2.49 | w |
| 41.65 | 2.16 | w |
| 44.57 | 2.03 | w |
| 47.48 | 1.91 | w |
| 49.53 | 1.83 | w |

This sample was calcined at 600° C. for 5 hrs under nitrogen and then air. The product resulting from the calcination was identified by x-ray diffraction (Rietveld refinement method described in J. Appl. Cryst. (1969) 2, 65-71) to be a mixture of 64.4 wt % MSE zeolite with a lattice parameter of 18.371 angstroms for a and 20.235 angstroms for c; 30.7 wt % MFI zeolite with a lattice parameter of 20.048 angstroms for a, 19.880 angstroms for b and 13.403 angstroms for c, and 4.8 wt % ERI zeolite with a lattice parameter of 13.071 angstroms for a and 15.238 angstroms for c. A 160 g portion of the calcined UZM-35 sample (Si/Al mole ratio 8.9) was NH4 exchanged. A solution was prepared by dissolving 160 g of NH₄NO₃ in 1800 g de-ionized water. The solution was heated to 75° C. before adding the calcined UZM-35. The slurry was stirred for 1 hr at 75° C. The product was isolated by filtration, washed with de-ionized water. This NH4 exchange procedure was repeated 3 times then it was dried at 100° C. for 12 hrs. Elemental analyses of this sample shows a Si/Al mole ratio to Si/Al=9.07, Na/Al=0.01, K/Al=0.11

Representative diffraction lines observed for the product are shown in Table 6.

TABLE 6

| 2θ | d (Å) | I/Io % |
|---|---|---|
| 6.67 | 13.22 | m |
| 6.97 | 12.65 | m-s |
| 7.94 | 11.12 | m |
| 8.14 | 10.85 | m |
| 8.93 | 9.88 | m |
| 9.79 | 9.01 | m-s |
| 10.92 | 8.09 | m |
| 13.78 | 6.42 | w |
| 14.1 | 6.27 | w |
| 14.97 | 5.91 | w |
| 15.7 | 5.63 | w |
| 16.05 | 5.51 | w |
| 17.57 | 5.04 | w |
| 19.64 | 4.51 | m |
| 20.05 | 4.42 | m |
| 20.65 | 4.29 | m |
| 21.13 | 4.19 | w |
| 21.77 | 4.07 | vs |
| 21.98 | 4.04 | s-vs |
| 22.62 | 3.92 | s |
| 23.14 | 3.84 | vs |
| 23.46 | 3.78 | m |
| 23.94 | 3.71 | m |
| 24.58 | 3.61 | w |
| 24.83 | 3.58 | w |
| 25.2 | 3.53 | m |
| 25.92 | 3.43 | w |
| 26.24 | 3.39 | m |
| 26.52 | 3.35 | m |
| 26.96 | 3.3 | m |
| 27.6 | 3.22 | m-s |
| 28.25 | 3.15 | m |
| 28.79 | 3.09 | m |
| 29.3 | 3.04 | m |
| 29.68 | 3 | w |
| 29.96 | 2.98 | m |
| 30.35 | 2.94 | m |
| 30.89 | 2.89 | m |
| 31.46 | 2.84 | m |
| 31.81 | 2.81 | m |
| 33.4 | 2.68 | m |
| 36.22 | 2.47 | w |
| 41.83 | 2.15 | w |
| 44.86 | 2.01 | w |
| 47.64 | 1.9 | w |
| 49.69 | 1.83 | w |

Example 9

An aluminosilicate reaction solution was prepared by first mixing 29.01 g of aluminum hydroxide (26.97% Al) and 483.08 g of dimethyldipropylammonium hydroxide (40.66% solution), while stirring vigorously. After thorough mixing, 461.58 g Ludox™ AS-40 (SiO₂, 40%) was added. The reaction mixture was homogenized for 20 minutes with a high-speed mechanical stirrer, the aluminosilicate colloidal solution was continuously stirred and an aqueous solution containing 27.90 g of KOH and 3.46 g of NaOH dissolved in 269.98 g H₂O, was added, drop wise, to the aluminosilicate solution. After the addition was completed, the resulting reaction mixture was homogenized for ½ hour, transferred to a 2000 ml Parr stainless steel autoclave, which was heated to 175° C. and maintained at that temperature for 10 days. The solid products were recovered by filtration, washed with de-ionized water, and dried at 100° C.

The product resulting from this reaction was identified by x-ray diffraction (Rietveld refinement method described in J. Appl. Cryst. (1969) 2, 65-71) to be a UZM-35 composition of 66.3 wt % MSE type zeolite with a lattice parameter of 18.369 angstroms for a and 20.284 angstroms for c; 25.5 wt % MFI with a lattice parameter of 20.136 angstroms for a, 19.976 angstroms for b and 13.443 angstroms for c, and 8.2 wt % ERI with a lattice parameter of 13.152 angstroms for a and 15.107 angstroms for c. Chemical analysis gave a product composition (mole ratio) of Si/Al=7.65, N/Al=0.38, K/Al=0.68, Na/Al=0.03. BET surface area was determined to be 404 m2/g and a micropore volume was 0.188 cc/g. Representative diffraction lines observed for the product are shown in Table 7.

TABLE 7

| 2θ | d (Å) | I/Io % |
|---|---|---|
| 6.48 | 13.32 | 31.9 |
| 6.78 | 13.02 | 58.5 |
| 8.05 | 10.96 | 25.7 |
| 8.71 | 10.13 | 33.6 |
| 9.61 | 9.18 | 53.6 |
| 10.75 | 8.21 | 11.2 |
| 13.61 | 6.49 | 12.9 |
| 14.74 | 6 | 7.3 |
| 15.86 | 5.58 | 7.2 |
| 19.48 | 4.55 | 41.5 |
| 19.9 | 4.45 | 21.1 |
| 20.5 | 4.32 | 13.4 |
| 20.96 | 4.23 | 25.6 |
| 21.61 | 4.1 | 100 |
| 21.81 | 4.07 | 63.8 |
| 22.42 | 3.96 | 45.7 |
| 22.94 | 3.87 | 85.5 |
| 23.3 | 3.81 | 38.5 |
| 23.5 | 3.78 | 31.3 |
| 23.86 | 3.72 | 17.8 |
| 24.41 | 3.64 | 6.8 |
| 25.78 | 3.45 | 20.2 |
| 26.09 | 3.41 | 19.8 |
| 26.81 | 3.32 | 39.8 |
| 27.14 | 3.28 | 20.9 |
| 27.44 | 3.24 | 42.9 |
| 27.69 | 3.21 | 33 |
| 28.06 | 3.17 | 14.7 |
| 29.15 | 3.06 | 16.2 |
| 29.55 | 3.01 | 13.5 |
| 29.86 | 2.98 | 20.8 |
| 30.14 | 2.96 | 18.7 |
| 30.75 | 2.9 | 24.1 |
| 31.26 | 2.85 | 8.9 |
| 33.21 | 2.69 | 11.1 |
| 34.34 | 2.6 | 8.8 |
| 34.76 | 2.57 | 10.5 |
| 35.2 | 2.54 | 6.8 |
| 35.57 | 2.52 | 8.6 |
| 36.02 | 2.49 | 8 |
| 41.71 | 2.16 | 9.8 |
| 44.61 | 2.02 | 8.2 |
| 47.48 | 1.91 | 8 |
| 49.56 | 1.83 | 10.1 |

This sample was calcined at 600° C. for 5 hrs under nitrogen and then air. The product resulting from the calcination was identified by x-ray diffraction (Rietveld refinement method described in J. Appl. Cryst. (1969) 2, 65-71) to be a UZM-35 composition of 61.9 wt-% MSE zeolite with a lattice parameter of 18.401 angstroms for a and 20.280 angstroms for c; 30.8 wt-% MFI zeolite with a lattice parameter of 20.114 angstroms for a, 19.919 angstroms for b and 13.432 angstroms for c, and 7.3-wt % ERI zeolite with a lattice parameter of 13.189 angstroms for a and 15.174 angstroms for c. A 100 g portion of the calcined UZM-35 sample (Si/Al mole ratio=7.65) was NH4 exchanged. A solution was prepared by dissolving 160 g of NH$_4$NO$_3$ in 1800 g de-ionized water. The solution was heated to 75° C. before adding the calcined UZM-35. The slurry was stirred for 1 hr at 75° C. The product was isolated by filtration, washed with de-ionized water. This NH4 exchange procedure was repeated 3 times then it was dried at 100° C. for 12 hrs. Elemental analyses of this sample shows a Si/Al mole ratio to Si/Al=9.20, Na/Al=0.01, K/Al=0.10.

Representative diffraction lines observed for the product are shown in Table 8.

TABLE 8

| 2θ | d (Å) | I/Io % |
|---|---|---|
| 6.5 | 13.58 | m |
| 6.81 | 12.95 | m |
| 7.98 | 11.07 | m |
| 8.76 | 10.08 | m |
| 9.63 | 9.16 | m |
| 10.77 | 8.2 | m |
| 13.63 | 6.48 | m |
| 14.8 | 5.98 | w |
| 15.84 | 5.58 | w |
| 19.51 | 4.54 | m |
| 19.91 | 4.45 | m |
| 20.49 | 4.32 | m |
| 21.01 | 4.22 | m |
| 21.62 | 4.1 | vs |
| 22.49 | 3.94 | s |
| 23.02 | 3.86 | vs |
| 23.3 | 3.81 | m-s |
| 23.64 | 3.76 | m |
| 23.91 | 3.71 | m |
| 24.41 | 3.64 | m |
| 24.62 | 3.61 | w |
| 25.11 | 3.54 | w |
| 25.81 | 3.44 | m |
| 26.09 | 3.41 | m |
| 26.41 | 3.37 | m |
| 26.86 | 3.31 | m-s |
| 27.45 | 3.24 | m-s |
| 27.65 | 3.22 | m |
| 28.13 | 3.16 | m |
| 28.82 | 3.09 | w |
| 29.14 | 3.06 | m |
| 29.57 | 3.01 | w |
| 29.84 | 2.99 | m |
| 30.21 | 2.95 | m |
| 30.76 | 2.9 | m |
| 31.31 | 2.85 | w |
| 33.27 | 2.69 | w |
| 36.12 | 2.48 | w |
| 41.68 | 2.16 | w |
| 44.74 | 2.02 | w |
| 47.56 | 1.91 | w |
| 49.57 | 1.83 | w |

The invention claimed is:

1. A process for alkylating aromatic hydrocarbons comprising contacting a hydrocarbon feedstock comprising at least alkylatable aromatics and a stream comprising olefins having from 2 to about 6 carbon atoms with a catalyst at alkylation conditions and producing an alkylated aromatic product wherein the catalyst comprises a UZM-35 microporous crystalline zeolitic composition comprising at least a MSE type zeolite, a MFI type zeolite, and an ERI type zeolite, wherein the UZM-35 composition has a three-dimensional framework of at least AlO$_2$ and SiO$_2$ tetrahedral units and an empirical composition in the as synthesized and anhydrous basis expressed by an empirical formula of:

where M represents a combination of potassium and sodium exchangeable cations, "m" is the mole ratio of M to (Al+E) and varies from about 0.05 to about 3, R is a singly charged dimethyldipropylammonium cation, "r" is the mole ratio of R to (Al+E) and has a value of about 0.25 to about 2.0, E is an element selected from the group consisting of gallium, iron, boron and mixtures thereof, "x" is the mole fraction of E and has a value from 0 to about 1.0, "y" is the mole ratio of Si to (Al+E)

and varies from greater than 2 to about 12 and "z" is the mole ratio of O to (Al+E) and has a value determined by the equation:

$$z=(m+r+3+4\cdot y)/2$$

and is characterized in that it has the x-ray diffraction pattern having at least the d-spacings and intensities set forth in Table A':

TABLE A'

| 2θ | d (Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w | and is thermally stable up to a temperature of at least 400° C.

2. The process of claim 1 where the alkylation conditions include a temperature of from 50° C. to 500° C., a pressure of from about 0 to 6895 kPag (about 0 to 1000 psig), an alkylatable aromatic to olefin mole ratio of from 10 to 0.1 and a contact time of from about 0.1 seconds to about 1 hour.

3. The process of claim 1 wherein the MSE type zeolite is present in an amount from about 55 wt % to about 90 wt. % of the UZM-35 composition.

4. The process of claim 1 wherein the MFI type zeolite is present in an amount from about 10 wt-% to about 35 wt-% of the UZM-35 composition.

5. The process of claim 1 wherein the ERI type zeolite is present in an amount from about 3 wt-% to about 10 wt-% of the UZM-35 composition.

6. The process of claim 2 wherein the UZM-35 composition is present with a binder in a proportion of about 5 to 100 mass-% zeolite and 0 to 95 mass-% binder.

7. The process of claim 1 where the alkylatable aromatic of the feedstock comprises an unsubstituted or monosubstituted benzene and where the olefin containing stream contains greater than 20 mol % ethylene and the alkylatable aromatic stream contains greater than 10 mol % benzene or monosubstituted benzene.

8. The process of claim 1 where the alkylatable aromatic of the feedstock comprises an unsubstituted or monosubstituted benzene and where the olefin containing stream contains greater than 50 mol % propylene and the alkylatable aromatic stream contains greater than 10 mol % benzene or monosubstituted benzene.

9. The process of claim 1 where the alkylatable aromatic is benzene and the olefin containing stream is propylene and where the alkylation conditions include a temperature of from 50° C. to 300° C., a pressure of from about 1378 to 5515 kPag (about 200 to 800 psig), a benzene to olefin mole ratio of from 10 to 0.3 and a contact time of from about 0.1 seconds to about 1 hour.

10. The process of claim 1 wherein "x" of the UZM-35 composition is zero.

11. The process of claim 1 where R is a combination of dimethyldipropyl ammonium hydroxide and at least one singly charged organoammonium cation selected from the group consisting of TEA, TPA, ETMA, DEDMA, trimethylpropylammonium, dimethyldiisopropyl ammonium, trimethylbutylammonium, dimethyldiethanolammonium, and methyltripropylammonium.

12. The process of claim 1 where the selectivity to monoalkylated products is greater than about 50 mol %.

13. An alkylation process comprising contacting a feedstock comprising unsubstituted or monosubstituted benzene and an olefin stream comprising ethylene with a catalyst at alkylation conditions and producing an alkylated aromatic product wherein the catalyst comprises a UZM-35 microporous crystalline zeolitic composition comprising at least a MSE type zeolite, a MFI type zeolite, and an ERI type zeolite, wherein the UZM-35 composition has a three-dimensional framework of at least $AlO_2$ and $SiO_2$ tetrahedral units and an empirical composition in the as synthesized and anhydrous basis expressed by an empirical formula of:

where M represents a combination of potassium and sodium exchangeable cations, "m" is the mole ratio of M to (Al+E) and varies from about 0.05 to about 3, R is a singly charged dimethyldipropylammonium cation, "r" is the mole ratio of R to (Al+E) and has a value of about 0.25 to about 2.0, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m+r+3+4\cdot y)/2$$

and is characterized in that it has the x-ray diffraction pattern having at least the d-spacing's and intensities set forth in Table A':

TABLE A'

| 2θ | d (Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |

| 2θ | d (Å) | I/Io % |
|---|---|---|
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w | and is thermally stable up to a temperature of at least 400° C.

14. The process of claim 13 wherein the alkylation conditions include a temperature of from about 50° C. to about 500° C., a pressure of from about 0 to about 6895 kPag (about 0 to about 1000 psig), an aromatic to olefin mole ratio of from about 10 to about 0.3 and a contact time of from about 0.1 seconds to about 1 hour.

15. The process of claim 1 wherein the MSE type zeolite is present in an amount from about 55 wt % to about 75 wt. % of the UZM-35 composition; the MFI type zeolite is present in an amount from about 20 wt-% to about 35 wt-% of the UZM-35 composition; and the ERI type zeolite is present in an amount from about 3 wt-% to about 9 wt-% of the UZM-35 composition.

16. The process of claim 13 where the aromatic feedstock is benzene and the selectivity to ethylbenzene is greater than about 50 mol %.

17. An alkylation process comprising contacting a feedstock comprising unsubstituted or monosubstituted benzene and an olefin stream comprising propylene with a catalyst at alkylation conditions and producing an alkylated aromatic product wherein the catalyst comprises a UZM-35 microporous crystalline zeolitic composition comprising at least a MSE type zeolite, a MFI type zeolite, and an ERI type zeolite, wherein the UZM-35 has a three-dimensional framework of at least $AlO_2$ and $SiO_2$ tetrahedral units and an empirical composition in the as synthesized and anhydrous basis expressed by an empirical formula of:

where M represents a combination of potassium and sodium exchangeable cations, "m" is the mole ratio of M to (Al+E) and varies from about 0.05 to about 3, R is a singly charged dimethyldipropylammonium cation, "r" is the mole ratio of R to (Al+E) and has a value of about 0.25 to about 2.0, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m+r+3+4\cdot y)/2$$

and is characterized in that it has the x-ray diffraction pattern having at least the d-spacing's and intensities set forth in Table A':

TABLE A'

| 2θ | d (Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w | and is thermally stable up to a temperature of at least 400° C.

18. The process of claim 17 where the alkylation conditions include a temperature of from about 50° C. to about 300° C., a pressure of from about 1378 to about 5515 kPag (about 200 to about 800 psig), an aromatic to olefin mole ratio of from about 10 to about 0.3 and a contact time of from about 0.1 seconds to about 1 hour.

19. The process of claim 1 wherein the MSE type zeolite is present in an amount from about 55 wt % to about 75 wt. % of the UZM-35 composition; the MFI type zeolite is present in an amount from about 20 wt-% to about 35 wt-% of the UZM-35 composition; and the ERI type zeolite is present in an amount from about 3 wt-% to about 9 wt-% of the UZM-35 composition.

20. The process of claim 17 wherein the aromatic feedstock is benzene and the selectivity to cumene is greater than 50 mol %.

* * * * *